(12) United States Patent
Dinsmore

(10) Patent No.: US 6,480,573 B1
(45) Date of Patent: Nov. 12, 2002

(54) THERAPEUTIC RADIATION SOURCE WITH INCREASED CATHODE EFFICIENCY

(75) Inventor: Mark Dinsmore, Sudbury, MA (US)

(73) Assignee: Photoelectron Corporation, North Billerica, MA (US)

( * ) Notice: Subject to any disclaimer, the term of this patent is extended or adjusted under 35 U.S.C. 154(b) by 0 days.

(21) Appl. No.: 10/005,287

(22) Filed: Dec. 4, 2001

(51) Int. Cl.$^7$ ................................................ H01J 35/06
(52) U.S. Cl. ........................................ 378/136; 378/119
(58) Field of Search .............................. 378/136, 119, 378/143, 138

(56) References Cited

U.S. PATENT DOCUMENTS

| | | | |
|---|---|---|---|
| 4,346,330 A | * 8/1982 | Lee et al. | 315/150 |
| 5,090,043 A | 2/1992 | Parker et al. | |
| 5,153,900 A | 10/1992 | Nomikos et al. | |
| 5,165,093 A | * 11/1992 | Miller et al. | 378/138 |
| RE34,421 E | 10/1993 | Parker et al. | |
| 5,369,679 A | 11/1994 | Sliski et al. | |
| 5,422,926 A | 6/1995 | Smith et al. | |
| 5,428,658 A | 6/1995 | Oettinger et al. | |
| 5,621,780 A | 4/1997 | Smith et al. | |
| 5,729,583 A | * 3/1998 | Tang et al. | 378/122 |
| 6,108,402 A | * 8/2000 | Chornenky | 378/119 |
| 6,319,188 B1 | 11/2001 | Lovoi | |
| 6,320,935 B1 | 11/2001 | Shinar et al. | |
| 6,324,257 B1 | 11/2001 | Halavee | |

FOREIGN PATENT DOCUMENTS

| | | |
|---|---|---|
| WO | WO 93/04735 | 3/1993 |
| WO | WO 01/47596 | 7/2001 |

* cited by examiner

*Primary Examiner*—Robert H. Kim
*Assistant Examiner*—Irakli Kiknadze
(74) *Attorney, Agent, or Firm*—McDermott, Will & Emery

(57) ABSTRACT

A therapeutic radiation source includes a optically heated thermionic cathode that is shaped so as to maximize the coupling efficiency of the incident optical radiation to the thermionic cathode. A fiber optic cable directs a beam of radiation, having a power level sufficient to heat at east a portion of the electron-emissive surface to an electron emitting temperature, from a laser source onto the cathode. An electron beam generated by said cathode strikes a target which is positioned in its beam path and which emits therapeutic radiation in response to incident accelerated electrons from the electron beam. The thermionic cathode has a non-planar configuration, such as a conical shape and a concave shape, adapted to allow an incident ray of optical radiation to impinge upon, and undergo absorption from, a plurality of regions within the surface of the cathode in succession.

17 Claims, 4 Drawing Sheets

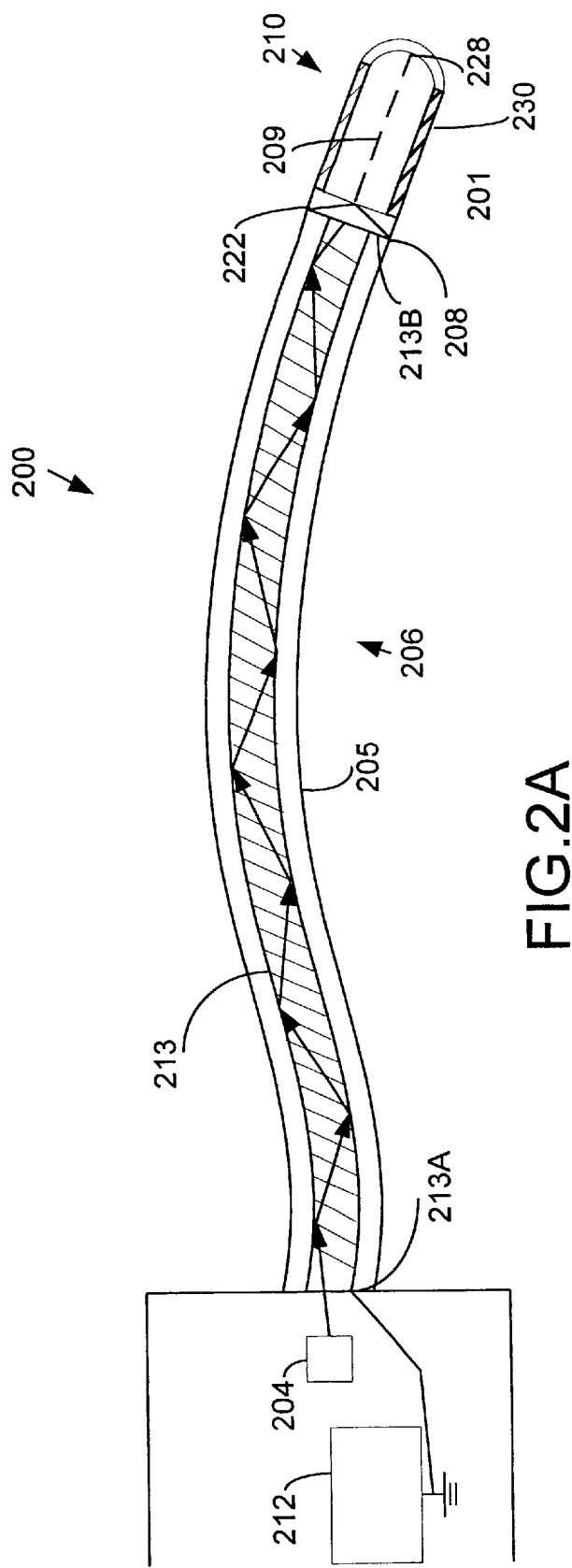

THERAPEUTIC RADIATION SOURCE WITH INCREASED CATHODE EFFICIENCY

CROSS-REFERENCE TO RELATED APPLICATIONS

Not Applicable

STATEMENT REGARDING FEDERALLY SPONSORED RESEARCH

Not Applicable

REFERENCE TO MICROFICHE APPENDIX

Not Applicable

FIELD OF THE INVENTION

The present invention relates to therapeutic radiation sources, and more particularly to a reduced power, increased efficiency miniaturized radiation source that utilizes an optically driven thermionic cathode.

BACKGROUND OF THE INVENTION

In the field of medicine, therapeutic radiation such as x-ray radiation and γ-ray radiation is used for diagnostic, therapeutic and palliative treatment of patients. The conventional medical radiation sources used for these treatments include large, fixed position machines as well as small, transportable radiation generating probes. The current state-of-the-art treatment systems utilize computers to generate complex treatment plans.

Conventional radiation systems used for medical treatment utilize a high power remote radiation source, and direct a beam of radiation at a target area, such as a tumor inside the body of a patient. This type of treatment is referred to as teletherapy because the radiation source is located a predefined distance from the target. This treatment suffers from the disadvantage that tissue disposed between the radiation source and the target is exposed to radiation. Teletherapy radiation sources, which apply radiation to target regions internal to a patient from a source external to the target regions, often cause significant damage not only to the target region or tissue, but also to all surrounding tissue between the entry site, the target region, and the exit site.

Brachytherapy, on the other hand, is a form of treatment in which the source of radiation is located close to or in some cases within the area receiving treatment. Brachytherapy, a word derived from the ancient Greek word for close ("brachy"), offers a significant advantage over teletherapy, because the radiation is applied primarily to treat only a predefined tissue volume, without significantly affecting the tissue adjacent to the treated volume. The term brachytherapy is commonly used to describe the use of radioactive "seeds," i.e. encapsulated radioactive isotopes, which can be placed directly within or adjacent the target tissue to be treated. Handling and disposal of such radioisotopes, however, may impose considerable hazards to both the handling personnel and the environment.

The term "x-ray brachytherapy" is defined for purposes of this application as x-ray radiation treatment in which the x-ray source is located close to or within the area receiving treatment. An x-ray brachytherapy system, which utilizes a miniaturized low power radiation source that can be inserted into, and activated from within, a patient's body, is disclosed in U.S. Pat. No. 5,153,900 issued to Nomikos et al., U.S. Pat. No. 5,369,679 to Sliski et al., and U.S. Pat. No. 5,422,926 to Smith et al., all owned by the assignee of the present application, all of which are hereby incorporated by reference.

The x-ray brachytherapy system disclosed in the above-referenced patents includes a miniaturized, insertable probe which is capable of generating x-ray radiation local to the target tissue, so that radiation need not pass through the patient's skin, bone, or other tissue prior to reaching the target tissue. The insertable probe emits low power x-rays from a nominal "point" source located within or adjacent to the desired region to be affected. In x-ray brachytherapy, therefore, x-rays can be applied to treat a predefined tissue volume without significantly affecting the tissue adjacent to the treated volume. Also, x-rays may be produced in predefined dose geometries disposed about a predetermined location. X-ray brachytherapy offers the advantages of brachytherapy, while avoiding the use and handling of radioisotopes. Also, x-ray brachytherapy allows the operator to control over time the dosage of the delivered x-ray radiation.

X-ray brachytherapy typically involves positioning the insertable probe into or adjacent to the tumor, or into the site where the tumor or a portion of the tumor was removed, to treat the tissue adjacent the site with a local boost of radiation. X-ray probes of the type generally disclosed in U.S. Pat. No. 5,153,900 include a housing, and a hollow, tubular probe or catheter extending from the housing along an axis and having an x-ray emitting target at its distal end. The probe may enclose an electron source, such as a thermionic cathode. In another form of an x-ray brachytherapy device, as disclosed in U.S. Pat. No. 5,428,658, an x-ray probe may include a flexible probe, such as a flexible fiber optic cable enclosed within a metallic sheath. In such a flexible probe, the electron source may be a photocathode. In a photocathode configuration, a photoemissive substance is irradiated by a LED or a laser source, causing the generation of free electrons. Typically, the flexible fiber optic cable couples light from a laser source or a LED to the photocathode.

It is possible to reduce the power requirements of miniaturized therapeutic radiation sources used in x-ray brachytherapy, by optically driving the thermionic cathodes in the electron sources, instead of ohmically heating the thermionic cathodes. U.S. patent application Ser. No. 09/884,561 (identified by Attorney Docket Nos. PHLL-155 and hereby incorporated by reference)(hereinafter the "PHLL-155" application) discloses a miniaturized therapeutic radiation source that includes a reduced-power, increased efficiency electron source that is optically driven. The PHLL-155 application discloses an electron source that includes a thermionic cathode having an electron emissive surface. The PHLL-155 application discloses using laser energy to heat the electron emissive surface of the thermionic cathode, instead of heating the electron emissive surface of the thermionic emitter using conventional ohmic heating. In this way, electrons can be produced in a quantity sufficient to produce the electron current necessary for generating therapeutic radiation at the target, while significantly reducing the power requirements for the therapeutic devices. Electrons can be generated with minimal heat loss, without requiring a vacuum-fabricated photocathode. By using optical heating, the mechanical complexity of the cathode is greatly reduced.

It is desirable that the surfaces of the thermionic cathodes be heated to as high a temperature as possible as quickly as possible, i.e. that the surfaces be heated as efficiently as possible. In order to reduce the power requirements for the miniature radiation source as disclosed in the PHLL-155 application, it is therefore necessary to minimize heat loss by the thermionic cathode. Heat loss by laser-heated thermionic cathodes generally includes 1) heat lost by thermal conduction; 2) heat loss caused by the portion of incident laser radiation that remains unabsorbed; and 3) heat loss by thermal radiation.

It is an object of this invention to increase the efficiency of a therapeutic radiation source having an optically driven thermionic cathode, by reducing the proportion of incident laser radiation that remains unabsorbed by the cathode. It is another object of this invention to increase the efficiency in the laser heating of a thermionic cathode in a miniaturized, laser-driven radiation source, by modifying the geometry and configuration of the cathode.

SUMMARY OF THE INVENTION

The present invention is directed to an optically driven therapeutic radiation source having a laser-heated thermionic cathode. In the present invention, the geometry and configuration of the thermionic cathode are designed to substantially increase the coupling efficiency of the incident laser radiation onto the cathode. This increase in coupling efficiency is achieved by substantially reducing the portion of incident laser radiation that remains unabsorbed by the cathode.

The present invention features a therapeutic radiation source that includes a radiation generator assembly, a source of optical radiation, and an optical delivery structure such as a fiber optic cable. The radiation generator assembly includes an electron source for emitting electrons to generate an electron beam along a beam path, and a target positioned in the beam path and adapted to emit therapeutic radiation in response to incident accelerated electrons from the electron beam. The electron source includes a thermionic cathode having an electron emissive surface. The fiber optic cable is adapted to transmit optical radiation, incident on an proximal end of the cable, to a distal end of the cable. The fiber optic cable directs a beam of the transmitted optical radiation upon the electron emissive surface of the cathode. The beam has a power level sufficient to heat at least a portion of the surface to an electron emitting temperature, so as to cause thermionic emission of the electrons from the surface.

The present invention features a non-planar configuration for the laser-heated thermionic cathode, in contrast to prior art themionic cathodes which have a planar, disk-shaped configuration. For example, the thermionic cathode may have a substantially conical shape, or a substantially convex shape, or a substantially hemispherical shape.

The thermionic cathode is shaped and designed so as to allow an incident beam of optical radiation to impinge upon, and undergo absorption from, a plurality of non-overlapping regions within the surface of the cathode, consecutively in succession. Because the incident optical radiation undergoes absorption processes from a plurality of regions within the surface, the amount of incident laser radiation that becomes absorbed by the non-planar thermionic cathode is substantially increased, as compared to the amount of incident radiation that is absorbed from only one region within a conventional planar, disk-shaped thermionic cathode. In other words, the coupling efficiency of the incident optical radiation to the thermionic cathode is substantially increased by modifying the shape and configuration of the cathode.

BRIEF DESCRIPTION OF THE DRAWINGS

FIG. 2A is an overall, diagrammatic view of one embodiment of a therapeutic radiation source constructed according to the present invention.

DETAILED DESCRIPTION

The present invention is directed to a miniaturized, low power therapeutic radiation source, which includes an electron-beam activated therapeutic radiation source, and which uses a laser-heated thermionic cathode. As described in the PHLL-155 application, using a laser-heated thermionic cathode, instead of a resistively heated thermionic cathode, significantly reduces the power requirements for such miniaturized therapeutic radiation sources. The present invention seeks to further reduce the power requirements for generating therapeutic radiation in the miniaturized radiation sources, by modifying the configuration of the thermionic cathode in such a way as to substantially reduce the portion of incident laser radiation that remains unabsorbed.

Figure 1:
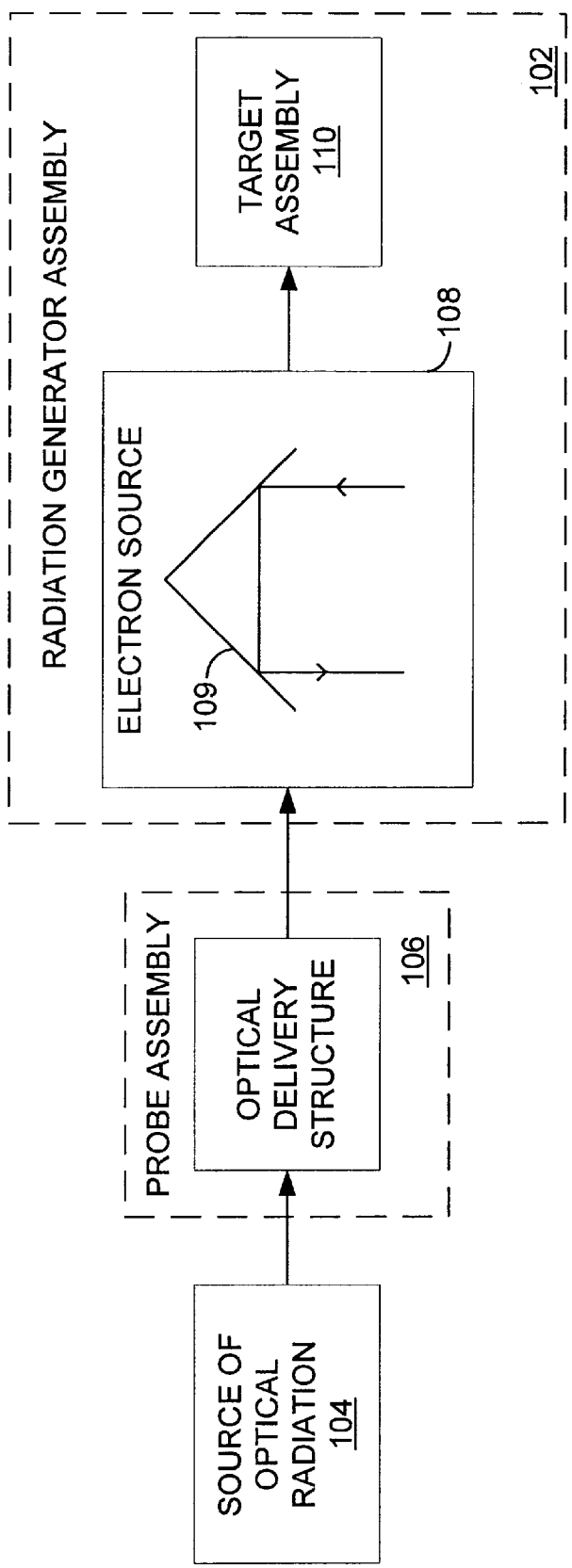
FIG. 1 is a schematic block diagram of an overview of one embodiment of a therapeutic radiation source, constructed in accordance with the present invention.

FIG. 1 is a schematic block diagram of an overview of one embodiment of a therapeutic radiation source 100, constructed according to the present invention, and including an optically heated thermionic cathode that is shaped to maximize the coupling efficiency of the incident optical radiation to the cathode. In overview, the system of the present invention includes a radiation generator assembly 102, a source of optical radiation 104, and a probe assembly 106. In a preferred embodiment, the source of optical radiation 104 is a laser, so that the optical radiation generated by the source is substantially monochromatic, and coherent. The laser may be a Nd:YAG laser, by way of example; however other lasers known in the art may be used, such as a diode laser and a molecular laser.

The radiation generator assembly 102 includes an electron source 108, and a target assembly 110 that includes means for emitting therapeutic radiation in response to incident accelerated electrons from the electron beam. The electron source 108 includes a conically-shaped thermionic cathode 109. The probe assembly 106 includes an optical delivery structure 112, such as a fiber optical cable assembly. The optical delivery structure 112 directs a beam of laser radiation generated by the laser 104 onto the electron source 108. The laser beam heats the thermionic cathode 109 in the electron source 108, so as to cause thermionic emission of electrons. In a preferred embodiment, the thermionic cathode has a non-planar configuration, adapted to allow a beam of incident optical radiation to impinge upon, and undergo absorption from, a plurality of non-overlapping regions within the surface of the cathode, in succession. In this way, the percentage of incident optical radiation that becomes absorbed by the cathode and that thereby becomes available for heating the cathode is substantially increased, thereby substantially increasing the coupling efficiency of the optical radiation to the cathode.

Generally, the apparatus of the present invention operates at voltages in the range of approximately 10 keV to 90 keV, and electron beam currents in the range of approximately 1 nA to 100 $\mu$A. At those operating voltages and currents, radiation output is relatively low, and the apparatus may be made small enough to be adapted for implantation in medical therapeutic applications. In view of the low-level radiation output, adequate tissue penetration and cumulative dosage may be attained by positioning the radiation source adjacent to or within the region to be irradiated. Thus, therapeutic radiation is emitted from a well-defined, small source located within or adjacent to the region to be irradiated.

Figure 2B:
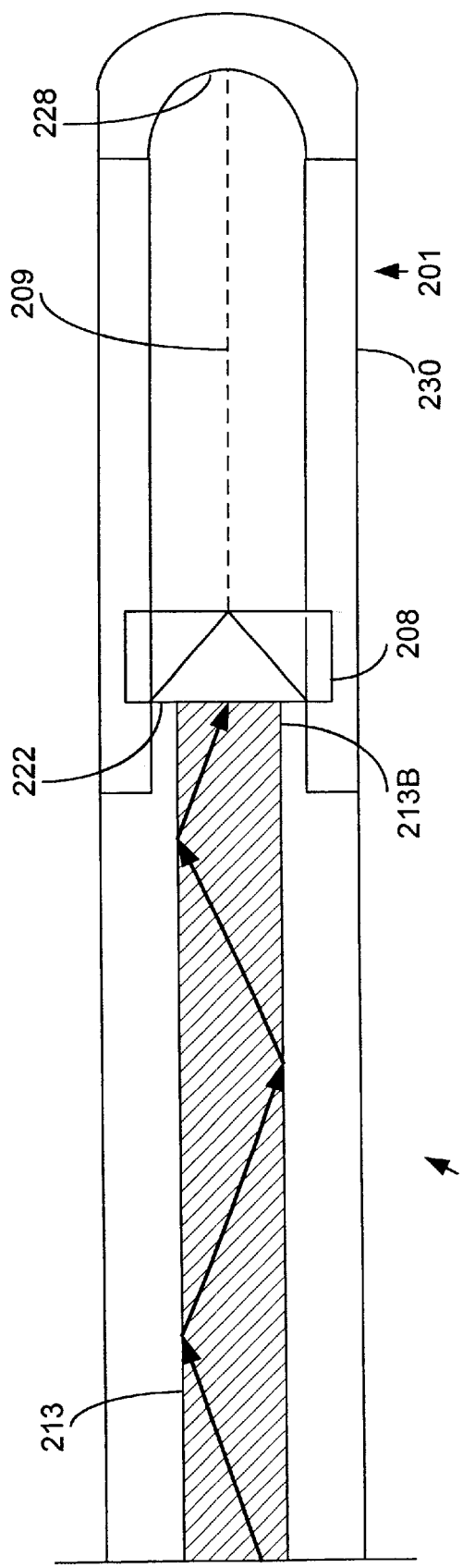
FIG. 2B provides an enlarged view of the radiation generator assembly, and the distal end of the probe assembly, constructed in accordance with the present invention.

FIGS. 2A and 2B show a diagrammatic view of one embodiment of the therapeutic radiation source apparatus 200 constructed according to the present invention. In the embodiment illustrated in FIG. 2A, the apparatus 200 includes a laser source 204, a probe assembly 206, and a radiation generator assembly 201. The radiation generator assembly 201 includes an electron source 208 that generates an electron beam along a beam path 209, and a target assembly 210 positioned in the beam path. In the illustrated embodiment, a high voltage power supply 212 is also provided. The probe assembly 206 couples both the laser source 204 and the high voltage power supply 212 to the target assembly 210. FIG. 2A provides an overall view of the therapeutic radiation source 200, whereas FIG. 2B provides an enlarged view of 1) the radiation generator assembly 201, and 2) the distal end of the probe assembly 206.

Referring to both FIGS. 2A and 2B, the electron source 208 includes a thermionic cathode 222 having an electron emissive surface. As mentioned earlier, the thermionic cathode 222 has a non-planar configuration that allows incident optical radiation to undergo absorption from a plurality of regions within the surface of the thermionic cathode 222. In a preferred embodiment, the thermionic cathode 222 has a substantially conical configuration. Other non-planar configurations, which allow an incident beam of optical radiation to consecutively hit a plurality of regions within the cathode surface, are within the scope of this invention. Such non-planar configurations include, but are not limited to, a substantially concave configuration, and a substantially hemispherical configuration.

The electron source 208 also includes means for establishing an accelerating electric field. In one embodiment, the means for establishing an accelerating electric field may be the high voltage power supply 212. The high voltage power supply 212 may establish an acceleration potential difference between the thermionic cathode 222 and the grounded target element 228, so that electrons emitted from the thermionic cathode 222 are accelerated toward the target element 228, and an electron beam is generated. The electron beam is preferably thin (e.g. 1 mm or less in diameter), and is established along a beam path 209 along a nominally straight reference axis that extends to the target assembly 210. The target assembly 210 is positioned in the beam path 209. The distance from the electron source 208 to the target assembly 210 is preferably less than 2–5 mm.

The high voltage power supply 212 preferably satisfies three criteria: 1) small in size; 2) high efficiency, so as to enable the use of battery power; and 3) independently variable x-ray tube voltage and current, so as to enable the unit to be programmed for specific applications. Preferably, the power supply 212 includes selectively operable control means, including means for selectively controlling the amplitude of the output voltage and the amplitude of the beam generator current. A high-frequency, switch-mode power converter can be used to meet these requirements. The most appropriate topology for generating low power and high voltage is a resonant voltage converter working in conjunction with a high voltage, Cockroft-Walton-type multiplier. Low-power dissipation, switch-mode power-supply controller-integrated circuits (IC) are currently available for controlling such topologies with few ancillary components. A more detailed description of the power supply 212 is provided in U.S. Pat. Nos. 5,153,900 and 5,428,658.

The target assembly 210 preferably includes a target element 228 spaced apart from and opposite the electron emissive surface of the thermionic cathode 222, where the target element 228 has at least one radiation emissive element adapted to emit therapeutic radiation in response to incident accelerated electrons from the electron emissive surface of the thermionic cathode 222. In a preferred embodiment, the emitted therapeutic radiation consist of x-rays, however it should be noted that the scope of this invention is not limited to x-rays, and other forms of therapeutic radiation may also be generated.

In one embodiment, the target element 228 is a small beryllium (Be) window, coated on the side exposed to the incident electron beam with a thin film or layer of a high-Z, x-ray emissive element, such as tungsten (W), uranium (U) or gold (Au). By way of example, when the electrons are accelerated to 30 keV-, a 2.2 micron thick tungsten layer absorbs substantially all of the incident electrons, while transmitting approximately 91% of any 30 keV-, 76% of any 20 keV-, and 67% of any 10 keV-x-rays generated in that layer. In this embodiment, the beryllium target element 228 is 0.5 mm thick. With this configuration, 95% of the x-rays generated in directions normal to and toward the target element 228, and having passed through the tungsten layer, are then transmitted through the beryllium window and outward at the distal end of the probe assembly 206.

In some forms of the invention, the target element 228 may include a multiple layer film, where the differing layers may have different emission characteristics. By way of example, the first layer may have an emission versus energy peak at a relatively low energy, and the second underlying layer may have an emission versus energy peak at a relatively high energy. With this form of the invention, a low energy electron beam may be used to generate x-rays in the first layer, to achieve a first radiation characteristic, and high energy electrons may be used to penetrate through to the underlying layer, to achieve a second radiation characteristic.

X-rays are generated in the target assembly in accordance with pre-selected beam voltage, current, and target element composition. The generated x-rays pass through the beryllium target substrate with minimized loss in energy. As an alternative to beryllium, the target substrate may be made of carbon or other suitable material which permits x-rays to pass with a minimum loss of energy. An optimal material for target substrate is carbon in its diamond form, since that material is an excellent heat conductor. Using these parameters, the resultant xrays have sufficient energy to penetrate into soft tissues to a depth of a centimeter or more, the exact depth dependent upon the x-ray energy distribution.

The radiation generator assembly 201, which can be for example 1 to 2 cm-in length, extends from the end of the probe assembly 206 and includes a capsule 230 which encloses the target assembly. According to one embodiment, the radiation generator assembly 201 is rigid in nature and generally cylindrical in shape. In this embodiment the cylindrical capsule 230 enclosing the radiation generator assembly 201 can be considered to provide a substantially rigid housing 230 for the electron source 208. In one embodiment, the electron source 208 and the target assembly 210 is disposed within the capsule 230, with the thermionic cathode disposed at an input end of the capsule 230, and the target assembly 210 disposed at an output end of the housing 230. The capsule 230 defines a substantially evacuated interior region extending along the beam axis 209, between the thermionic cathode 222 at the input end of the capsule 230 and the target assembly 210 at the output end of the housing 230. The inner surface of the radiation generator assembly 201 is lined with an electrical insulator, while the external surface of the assembly is electrically conductive. According to a preferred embodiment, the radiation generator assembly 201 is hermetically sealed to the end of the probe assembly, and evacuated. According to another embodiment, the entire probe assembly 206 is evacuated.

The probe assembly 206 couples the laser source 204 and the high voltage power supply 212 to the target assembly 210. In the illustrated embodiment, the probe assembly 206 includes a flexible, electrically conductive catheter 205 extending along a probe axis between a proximal end and a distal end of the catheter 205. The probe assembly 206 includes optical delivery structure 213 having a proximal end 213A and a distal end 213B. The distal end 213B of the optical delivery structure 213 is affixed to the radiation generator assembly 201.

In a preferred embodiment, the optical delivery structure 213 is a flexible fiber optical cable. In this embodiment, the flexible catheter 205 that encloses the fiber optical cable 202 is a small-diameter, flexible, metallic outer tube. In this embodiment, the target assembly 210 includes an electrically conductive outer surface. Preferably, both the metallic tube 205 and the target element 228 are set at ground potential, in order to reduce the shock hazard of the device. In one embodiment, the fiber optical cable has a diameter of about 200 microns, and the flexible metallic tube 205 has a diameter of about 1.4 mm.

In a preferred embodiment, the fiber optic cable 213 includes an electrically conductive outer surface. For example, the outer surface of the fiber optic cable 213 may be made conductive by applying an electrically conductive coating. The electrically conductive outer surface of the fiber optic cable 213 provides a connection to the thermionic cathode 222 from the high voltage power supply 212. In this embodiment, the radiation generator assembly 201 also has an electrically conductive outer surface. Preferably, both the flexible metallic sheath 205 and the outer conductive surface of the radiation generator assembly 201 are set at ground potential, in order to reduce the shock hazard of the device. The flexible sheath 205 couples a ground return from the target element 228 to the high voltage power supply 212, thereby establishing a high voltage field between the thermionic cathode 222 and the target element 228. In an exemplary embodiment, the fiber optic cable 213 may have a diameter of about 200 microns, and the flexible metallic sheath 205 may have a diameter of about 1.4 mm. A layer of dielectric material provides insulation between the outer surface of the fiber optic cable 213 and the inner surface of the metallic sheath 205.

Getters may be positioned within the housing 230. The getters aid in creating and maintaining a vacuum condition of high quality. The getter has an activation temperature, after which it will react with stray gas molecules in the vacuum. It is desirable that the getter used have an activation temperature that is not so high that the x-ray device will be damaged when heated to the activation temperature.

The thermionic cathode 222 has an electron emissive surface, and is typically formed of a metallic material. Suitable metallic materials forming the cathode 222 may include tungsten, thoriated tungsten, other tungsten alloys, and tantalum. In one embodiment, the cathode 222 may be formed by depositing a layer of electron emissive material on a base material, so that an electron emissive surface is formed thereon. By way of example, the base material may be formed from one or more metallic materials, including but not limited to Group VI metals such as tungsten, and Group II metals such as barium. In one form, the layer of electron emissive material may be formed from materials including, but not limited to, aluminum tungstate and scandium tungstate. The thermionic cathode 222 may also be an oxide coated cathode, where a coating of the mixed oxides of barium and strontrium, by way of example, may be applied to a metallic base, such as nickel or a nickel alloy. The metallic base may be made of other materials, including Group VI metals such as tungsten. The thermionic cathode 222 has a nonplanar configuration, designed to maximize the percentage of incident laser radiation that actually becomes absorbed by the thermionic cathode surface.

The fiber optical cable 202 is adapted to transmit laser radiation, generated by the laser source 204 (shown in FIG. 2(a)) and incident on the proximal end of the fiber optical cable assembly, to the distal end of the fiber optical cable assembly 213. The fiber optical cable 202 is also adapted to deliver a beam of the transmitted laser radiation to impinge upon the electronemissive surface of the thermionic cathode 222. The beam of laser radiation must have a power level sufficient to heat at least a portion of the electron-emissive surface to an electron emitting temperature so as to cause thermionic emission of electrons from the surface.

In operation, the laser beam shining down the fiber optic cable 213 impinges upon the surface of the thermionic cathode 222, and rapidly heats the surface to an electron emitting temperature, below the melting point of the metallic cathode 222. Upon reaching of the surface of a electron emitting temperature, electrons are thermionically emitted from the surface. The high voltage field between the cathode 222 and the target element 228 (shown in FIGS. 2A and 2B accelerates these electrons, thereby forcing them to strike the surface of the target element 228 and produce x-rays. In one embodiment of the invention, a Nd:YAG laser was coupled into a SiO2 optical fiber having a diameter of 400 microns. A 20 kV power supply was used, and a thermionic cathode made of tungsten was used. With a conventional disc-shaped, planar cathode, just a few watts of power was needed to generate over 100 $\mu$A of electron current. In one example, an infrared diode laser was used to achieve about 100 $\mu$A of electron current, with only 180 mW of power, using a disc-shaped cathode. Using a conically-shaped cathode, or cathodes having different non-planar configurations, further reduces the power requirements for the present invention, as discussed in conjunction with FIG. 3A and 3B below.

Figure 3A:
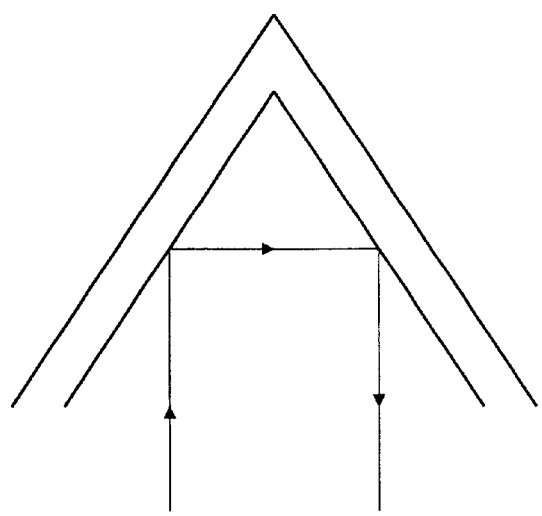
FIGS. 3A and 3B show a thermionic cathode constructed in accordance with the present invention and having a non-planar configuration adapted to increase the coupling efficiency of the incident optical radiation to the cathode.
Figure 3B:
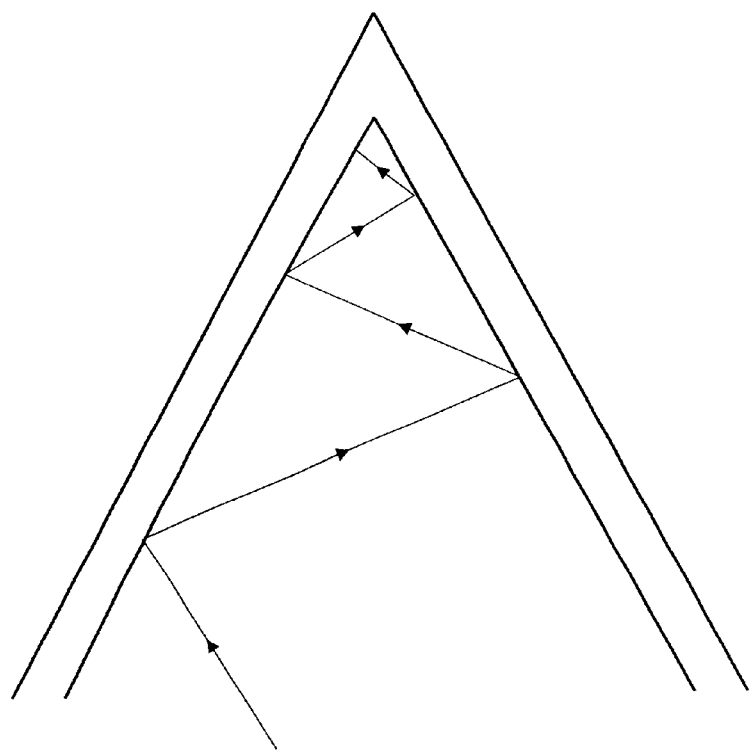

FIGS. 3A and 3B illustrate in more detail a conically-shaped cathode constructed in accordance with the present invention. For a disc-shaped or planar thermionic cathode, the percentage of incident radiation that is absorbed at an incident region on the cathode is typically about 40%. With a non-planar, conically shaped cathode, as illustrated in FIGS. 3A and 3B, the portion of the incident laser energy that remains unabsorbed can be significantly reduced.

In the present invention, the thermionic cathode is constructed so as to allow an incident beam of optical radiation to consecutively impinge upon a plurality of non-overlapping regions within the surface of the cathode, so as to substantially increase the percentage of incident radiation that is retained and absorbed by the cathode. In other words, an incident beam of optical radiation undergoes a plurality of reflection processes, as well as a plurality of absorption processes, from the surface of the cathode, before substantially reversing direction. Each additional region of the surface, upon which the incident beam impinges, becomes an additional absorption site for the light that is incident thereupon. In this way, the coupling efficiency of the incident radiation to the thermionic cathode is substantially increased, as compared to the coupling efficiency achieved with planar cathodes, from which the incident radiation undergoes only one absorption process, before reversing direction.

In one embodiment of the invention, the thermionic cathode may have a substantially conical shape, as shown in FIGS. 3A and 3B. In the embodiment illustrated in FIG. 3A, the incident beam of optical radiation impinges upon a first region 310 of the cathode, at an angle of incidence theta. The incident optical radiation undergoes partial absorption at the region 310. Typically, about 40% of the incident radiation is absorbed. The remaining 60% of the incident radiation is reflected, at an angle of reflection thetar that is substantially equal to the angle of incidence thetai. The conical configuration of the thermionic cathode permits the portion of the incident radiation reflected at the region 310, i.e. about 60% of the incident radiation, to impinge upon, and to undergo a second absorption process from, a second region 312 within the surface of the thermionic cathode. Another 40% of the 60%, i.e. about 24% of the incident radiation, is further absorbed from the region 312. The portion of the incident radiation that remains absorbed by the thermionic cathode, and becomes available for heating the cathode, is thus 64%, in contrast to 40% in conventional, planar cathodes.

In the embodiment illustrated in FIG. 3B, the incident beam of optical radiation impinges upon, and undergoes absorption from, regions 420, 422, 424, and 426 within a thermionic cathode 400. About 40% of the incident radiation is absorbed at region 420, about 24% is absorbed at region 422, about 6% is absorbed at region 424, and about 2% is absorbed at region 426. As there is no geometrical reflection path that allows the beam to escape, virtually all the optical power is absorbed.

Besides the conical configuration illustrated in FIGS. 3A and 3B, other shapes and configurations may be used that allow for a plurality of consecutive absorption processes at a plurality of non-overlapping regions within the cathode. For example, in one embodiment of the invention (not shown), the thermionic cathode may have a substantially hemispherical shape. In yet another embodiment of the invention, the thermionic cathode may have a substantially concave shape. In such an embodiment of the invention (not shown), the thermionic cathode may include an intersection edge and a first and a second substantially flat surface, each surface having a distal end and extending outward from the intersection edge toward its distal end. The first surface and the second surface form an angle with respect to each other, and allow an incident ray of optical radiation to successively impinge upon, and undergo absorption from, the first surface and the second surface alternatingly, in succession.

By shaping the thermionic cathode so as to allow the incident radiation to undergo a plurality of absorption processes at a plurality of non-overlapping regions within the cathode, the present invention allows for a substantial increase in the coupling efficiency of the incident optical radiation to the thermionic cathode. The power requirements for an optically driven therapeutic radiation source, as featured in the present invention, are thereby substantially reduced.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A therapeutic radiation source, comprising:
   A. a radiation generator assembly, comprising:
      a. an electron source for emitting electrons to generate an electron beam along a beam path, said electron source including a thermionic cathode having an electron emissive surface, and
      b. a target positioned in said beam path, said target including means for emitting therapeutic radiation in response to incident accelerated electrons from said electron beam;
   B. a source of optical radiation; and
   C. an optical delivery structure having a proximal end and a distal end and adapted for transmitting to said distal end optical radiation generated by said source and incident on said proximal end;
      wherein said optical delivery structure is adapted for directing a beam of said transmitted optical radiation upon a surface of said cathode, said beam of optical radiation having a power level sufficient to heat at least a portion of said surface to an electron emitting temperature so as to cause thermionic emission of electrons from said surface; and
      wherein said cathode has a non-planar configuration and is constructed and arranged so as to allow an incident beam of optical radiation to consecutively impinge upon a plurality of non-overlapping regions within the surface of the cathode so that said incident beam of optical radiation undergoes a corresponding plurality of absorption processes from said surface in succession.

2. A therapeutic radiation source according to claim 1, wherein said thermionic cathode includes an intersection edge and at least a first and a second substantially flat surface, each surface having distal end and extending outward from said intersection edge toward said distal end;
   wherein said first surface and second surface form an angle with respect to each other, and are adapted to allow an incident ray of optical radiation to successively impinge upon, and undergo absorption from, said first surface and said second surface alternatingly and in succession.

3. A therapeutic radiation source according to claim 1, wherein said thermionic cathode has a substantially conical shape.

4. A therapeutic radiation source according to claim 1, wherein said thermionic cathode has a substantially concave shape.

5. A therapeutic radiation source according to claim 1, wherein said thermionic cathode has a substantially hemispherical shape.

6. A therapeutic radiation source according to claim 1, further comprising:
   a substantially rigid housing enclosing said thermionic cathode and said target, wherein said housing defines a substantially evacuated interior region extending along said beam path between an input end and an output end of said housing.

7. A therapeutic radiation source according to claim 1, wherein said thermionic cathode is disposed at said input end of said housing.

8. A therapeutic radiation source according to claim 1, further comprising a radiation transmissive window at an output end of said housing, wherein therapeutic radiation emitted from said target is directed through said radiation transmissive window.

9. A therapeutic radiation source according to claim 1, wherein said optical delivery structure comprises a fiber optical cable.

10. A therapeutic radiation source according to claim 1, wherein said fiber optical cable has a diameter between about 100 microns to about 200 microns.

11. A therapeutic radiation source according to claim 1, wherein the power required for heating said electron emissive surface of said cathode so as to generate an electron beam forming a current of about 100 $\mu$A is between about 0.1 Watt to about 1.0 Watt.

12. A therapeutic radiation source according to claim 1, wherein said optical source is a laser, and wherein said beam of optical radiation is substantially monochromatic and coherent.

13. A therapeutic radiation source according to claim 1, wherein said therapeutic radiation comprises x-rays.

14. A therapeutic radiation source according to claim 1, wherein the percentage of incident optical radiation that becomes absorbed by said thermionic cathode is between about 40% and about 100%.

15. A therapeutic radiation source according to claim 1, further including means for providing an accelerating voltage between said electron source and said target element so as to establish an accelerating electric field which acts to accelerate electrons emitted from said electron source toward said target element.

16. A therapeutic radiation source according to claim 15, wherein said means for establishing an accelerating electric field is a power supply.

17. A therapeutic radiation source, comprising:
A. a radiation generator assembly, comprising:
   a. an electron source for emitting electrons to generate an electron beam along a beam path, said electron source including a thermionic cathode having an electron emissive surface, and
   b. a target positioned in said beam path, said target including means for emitting therapeutic radiation in response to incident accelerated electrons from said electron beam; and
   c. a substantially rigid housing enclosing said thermionic cathode and said target, wherein said housing defines a substantially evacuated interior region extending along said beam path between an input end and an output end of said housing.
B. a source of optical radiation; and
C. optical delivery structure having a proximal end and a distal end and adapted for transmitting to said distal end optical radiation generated by said source and incident on said proximal end, said optical delivery structure being adapted for directing a beam of said transmitted optical radiation upon a surface of said thermionic cathode, wherein said beam of optical radiation has a power level sufficient to heat at least a portion of said surface to an electron emitting temperature so as to cause thermionic emission of electrons from said surface; and
wherein said thermionic cathode has a non-planar configuration adapted to allow incident optical radiation to undergo a plurality of absorption processes from a plurality of regions within said surface in succession.

* * * * *